(12) United States Patent
Herraez et al.

(10) Patent No.: US 8,228,078 B2
(45) Date of Patent: Jul. 24, 2012

(54) METHOD AND DEVICE FOR MONITORING AND DETECTING THE COATING DEFECTS OF UNDERGROUND OR UNDERWATER PIPELINES

(75) Inventors: Carlos Herraez, Madrid (ES); Alvaro Aballe, Madrid (ES)

(73) Assignee: EUPEC Pipeline Services España, S.A.U., Madrid (ES)

( * ) Notice: Subject to any disclaimer, the term of this patent is extended or adjusted under 35 U.S.C. 154(b) by 542 days.

(21) Appl. No.: 11/989,571

(22) PCT Filed: Jul. 25, 2006

(86) PCT No.: PCT/DE2006/001317
§ 371 (c)(1), (2), (4) Date: May 12, 2010

(87) PCT Pub. No.: WO2007/012326
PCT Pub. Date: Feb. 1, 2007

(65) Prior Publication Data
US 2010/0213955 A1    Aug. 26, 2010

(30) Foreign Application Priority Data

Jul. 29, 2005 (DE) .......................... 10 2005 036 508

(51) Int. Cl.
*G01R 27/08* (2006.01)
*G01N 27/00* (2006.01)
(52) U.S. Cl. .......................... 324/705; 324/718; 324/71.2
(58) Field of Classification Search .................. None
See application file for complete search history.

(56) References Cited

U.S. PATENT DOCUMENTS

| | | | |
|---|---|---|---|
| 4,471,294 A * | 9/1984 | Nielsen .......................... | 324/534 |
| 4,940,944 A | 7/1990 | Steele et al. | |
| 5,180,969 A * | 1/1993 | Kwun et al. .................. | 324/71.2 |
| 5,331,286 A | 7/1994 | Rivola et al. | |

FOREIGN PATENT DOCUMENTS

| | | |
|---|---|---|
| DE | 690 14 002 T2 | 5/1995 |
| EP | 0 560 443 B1 | 9/1993 |
| EP | 1 152 235 A1 | 11/2001 |
| WO | WO 2004/097460 A1 | 11/2004 |

OTHER PUBLICATIONS

Written Opinion in International Patent Application No. PCT/DE2006/001317, having a mailing date of Apr. 16, 2007.
W. von Baeckmann, W. Schwenk, and W. Prinz (Editors), *Handbook of Cathodic Corrosion Protection*, $3^{rd}$ Edition, pp. 112-124, published 2007 by Elsevier Science, Burlington, MA, USA.
International Search Report in PCT/DE2006/001317 having a mailing date of Jan. 11, 2007.
International Preliminary Report on Patentability in PCT/DE2006/001317, date of completion of report of Oct. 2, 2007, with English translation of International Preliminary Report on Patentability obtained from WIPO Patentscope® website.

* cited by examiner

*Primary Examiner* — Paresh Patel
(74) *Attorney, Agent, or Firm* — O'Brien Jones PLLC

(57) ABSTRACT

A method for monitoring and detecting coating defects in a defined section of a coated underground or underwater pipeline provided with a monitoring unit fixedly mounted by sections and at the end of the respective section and an apparatus used in the method.

13 Claims, 1 Drawing Sheet

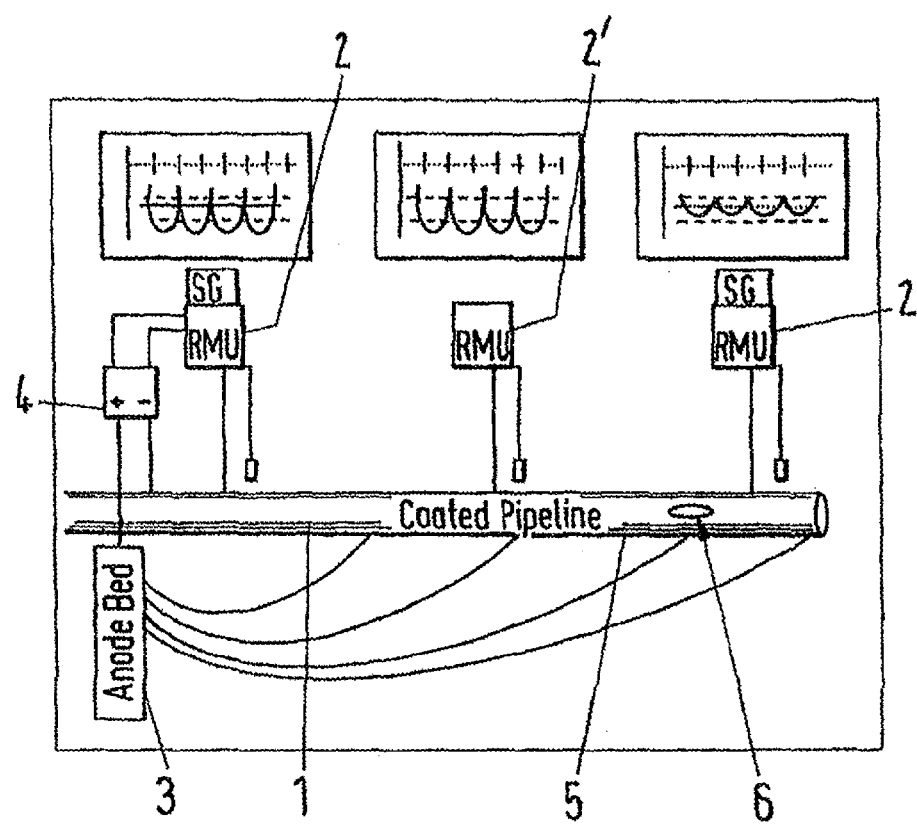

METHOD AND DEVICE FOR MONITORING AND DETECTING THE COATING DEFECTS OF UNDERGROUND OR UNDERWATER PIPELINES

This application is a 371 of PCT/DE2006/001317 filed Jul. 25, 2006.

FIELD OF THE DISCLOSURE

The invention relates to a method and device for monitoring and detecting coating defects on underground or underwater pipe-lines according patent claims 1 and 9.

BACKGROUND OF THE DISCLOSURE

Depending on the magnitude and type of risk, pipe lines subject to corrosion risks are protected by a passive or active protection system or a combination of both. The passive protection is comprised of a coating, the active protection is either a cathodic protection or a protection via a so-called sacrificial anode.

The coating must be electrically insulating in order to avoid direct contact of the pipe line with the electrically conducting medium 'ground' or 'water' and therewith a corrosive attack on the pipe line.

In the case of cathodic corrosion protection of underground pipe lines provided with an electrically insulating coating the pipe line is protected against corrosion at surface defects of the insulating encasing thereby that to the pipe line a DC voltage is so connected that the pipe line has an electrically negative potential with respect to the surrounding soil, or acts as a cathode. For this purpose the negative pole of a DC voltage source is connected to the pipe line and its positive pole, or the anode, is grounded.

The active protection can alternatively also take place by way of applying so-called sacrificial anodes to the pipe line. The basic principles are described, for example, in the *Handbuch des kathodischen Korrosionsschutzes*, VCH Verlag, Third Edition 1989.

The effectiveness of the passive protection of the pipe line via the coating is a function of the quality, i.e. the freedom from defects, of the coating. Damages on the coating, which cause an electric contact of the pipe with the soil or the water, lead to a corrosive attack on steel pipes to be protected, which can result in large-area delaminations of the coating. The extent of delamination depends herein on the type of coating system and the obtaining corrosion conditions (for example conductivity of the ground, pH-value, etc.).

Damage to the coating can occur, for example, during the transport of the pipe such that before laying the pipe the coating is customarily inspected for defects and the sites of the defect are repaired.

However, the coating can also be damaged during the operation of the pipe line, for example during earth work carried out in the proximity of a laid pipe line, through microbiological attacks or settlements and shifts in the ground.

This requires that the pipe line is regularly checked for potential damage of the coating in order to avoid greater corrosion damage, which is especially important in the case of pipe lines carrying oil or gas, in order to prevent leakages due to corrosion damage.

Relatively frequent line inspections are, however, not acceptable for economic reasons since the measurements are complex and expensive.

Methods for locating defects known in prior art are described, for example in *Handbuch des kathodischen Korrosionsschutzes*, VCH Verlag, Third Edition, 1989, pp. 112-124. Conventionally, in this method from the trace-form of the protective current and the potential in defined line sections conclusions are drawn regarding possible damage in the coating.

A further method based on measurements of the shape of the potential and the determination of the resistance of the coating over a modulated cathodic protective current is disclosed in DE 690 14 002 T2.

Of disadvantage in these known methods is, however, that, for example in the pipe line sections to be examined, signals from current-carrying lines crossing the pipe line are also acquired and the acquired signal indications can no longer be uniquely assigned to a possible coating defect. The reason is that the analyzed current trace is composed of the fed protective current and the external current signal.

Of disadvantage is, furthermore, that these methods can only be applied in combination with a cathodic protection of the pipe line.

EP 0560 443 B1 discloses a method for monitoring and localizing damages on the coating of a cathodically protected underground pipe line, in which by applying superimposed local sinusoidal exciting currents of different frequencies to the pipe line and measuring the corresponding voltage responses or the impedance, possible damages are detected. Herein with a mobile measuring system the pipe line is examined in constant 2 meter long sections for possible damages of the coating.

This method has several disadvantages. For one, the method can also only be applied in combination with a cathodic protective device. Furthermore, it cannot be excluded that via external effects interference signals are also acquired and therewith a unique defect assignment is no longer possible. Furthermore, it is disadvantageous that for the application of this method an examination directly on the pipe is required, which is highly time-consuming and expensive in long pipe lines to be tested.

SUMMARY OF THE DISCLOSURE

The invention addresses the problem of specifying a reliable and cost-effective method for monitoring and detecting coating defects in a defined section of an underground or underwater pipe line, which method can be applied independently of active corrosion protection methods and in which the further disadvantages of the methods known so far are avoided.

This problem is solved according to the invention thereby that the method comprises the following steps:

Applying under clocked cycling an AC current signal whose fixedly predetermined and stable frequency, taking into consideration the tolerance, in comparison to the frequencies measured within the scope of the monitoring of possible external interference signals is distinctly different Acquiring the wave form of the AC current signal in the two terminal monitoring units of the particular section to be monitored for the determination of the distance-dependent attenuation level as a function of the distance of the signal from the location of the impressing with this signal Conversion of the time-dependent signal into a frequency-dependent signal Determination of the frequency amplitudes corresponding to the frequency of the AC current signal Determination of the attenuation level of the frequency amplitudes within the pipe line section to be monitored and comparison with comparison values previously determined in both terminal monitoring units.

The great advantage of the method according to the invention comprises that therewith it becomes feasible to examine coated pipe lines located underground as well as also underwater even if they are not actively protected for coating damages. This method can advantageously also be utilized for the remote monitoring of pipe lines such that complex and expensive examinations onsite become superfluous.

It is furthermore advantageous to make possible via the determination of the attenuation level of the AC current signal placed onto the pipe line the monitoring of even longer line pipe sections, for example up to 50 km, in simple, cost-effective and reliable manner.

In the case of cathodically protected pipe lines which are provided section-wise with monitoring units for the cathodic protective current, the acquisition unit required for the AC current signal to be applied can advantageously be integrated in simple manner into the monitoring unit for the protective current monitoring. Herein the cathodic protective current is advantageously superimposed by the AC current signal and analyzed separately.

The signals acquired by the monitoring unit can subsequently advantageously be transmitted either via already laid ground cables or wirelessly via radio, GPS or satellite transmission to the central monitoring station and, if needed, be further evaluated.

The method according to the invention is based on the physical effect that the voltage or current amplitudes of an AC current signal are attenuated as a function of the distance from the site of its impression on the pipe line section. For this purpose at certain distances signal generators are applied on the pipe line, which signal generators impress the pipe line with an AC current signal. The further removed the measuring site is from the site of the impressing of the additional current signal, the more strongly attenuated are the amplitude signals. If there are defects in the coating which establish an electric contact from the line section of the pipe to the ground, such defects are evident in a characteristic signal indication in the level of attenuation and can consequently be uniquely assigned to this pipe line section.

Based on the level of the previously determined attenuation in the defect-free line section in comparison to the determined actual attenuation, the site of the defect can be narrowed down with satisfactory accuracy in relation to the distance from the site of the impression of the signal. In order to be able to appraise the damaged region and to be able to initiate corresponding measures, the damaged site is subsequently located exactly through suitable onsite measurements.

BRIEF DESCRIPTION OF THE DRAWINGS

FIG. 1 is an illustration of a system according to the present disclosure.

MORE DETAILED DESCRIPTION

In the method according to the invention, first, the wave form of the AC current signal in the two terminal monitoring units of the particular section to be monitored is acquired as a function of the distance of the signal from the site of the impression with this signal and the time-dependent signal is converted into a frequency-dependent signal.

The attenuation determined herefrom of the frequency amplitudes is subsequently compared with the previously determined attenuation of a comparison signal such that possible discrepancies can be assigned to a coating defect.

On the basis of the measurements performed at specific time intervals from the magnitude of the time change of these attenuation discrepancies can be determined whether or not there is a coating defect on the pipe line.

In principle, a very broad frequency spectrum can be considered for the selection of a suitable superposition frequency in order to obtain various information about the condition of the coating. Low frequencies, for example, are better suited for detecting damage on the coating itself, while higher frequencies are better suited for detecting coating detachments from steel surfaces.

The maximal frequency is limited by the indication range of the signal, which depends on the length of the pipe section to be tested. Furthermore, the quality and type of the coating affect the indication range.

The minimal frequency is limited by a still sufficient signal-to-noise ratio. The optimal frequency of the AC current signal depends, for one, on the measuring frequency, for another also on the level of attenuation over the length of the pipe section and the signal-to-noise ratio.

The best superposition frequency to be selected will therefore be a compromise between the indication range of the signal and the signal-to-noise ratio.

However, in any event it is essential that the frequency of the AC current signal is markedly different from the frequencies, or their harmonics, of interference signals, such as, for example, are induced by crossing power lines. Only hereby is a unique assignment to a potential defect in the monitored pipe line section possible.

In power lines the frequencies of these interference signals are, for example, 50 or 60 Hz. For the detection of coating damage for this case, for example, good results are achieved with a frequency of 130 Hz.

For the above described reasons, in practice frequencies lower than 1 Hz and frequencies higher than 1000 Hz are virtually not suitable.

A further aspect to be considered can also comprise selecting a frequency which can be processed with conventional cost-effectively available A/D converters.

The AC current signal itself is advantageously sinusoidal in order to facilitate the succeeding transformation of the time signal into a frequency signal of the digitized signals, for example, by Fourier transformation. Other signal forms, for example rectangular, are in principle also possible.

A further advantage of the method according to the invention comprises that, even in the case of cathodically protected pipe lines, the monitoring unit for damage to the coating can also be added if necessary and independently of time, for example once a day.

Since the length of the measuring cycle proper for the AC current signal is in the range of seconds or even lower, in combination with the monitoring of the signals from a central station highly effectively and rapidly a comprehensive, cost-effective and reliable monitoring of the entire pipe line can take place in this manner and damages on the coating can be detected in a timely manner.

When utilizing several signal generators for the length of the pipe line, wherein each signal generator can involve several pipe line sections, it is necessary for the quality and level of confidence of the measurement of the AC current signal that in each instance always only one signal generator for the particular measurement is switched on. Since the signal generators send out the current signal at both sides of the pipe line section, the signal to be evaluated would otherwise possibly be superimposed by further signals of other signal generators, and the result would therewith be falsified. It is therefore important that the signal generators are either so programmed that with each measurement always only one signal generator is active or a further active signal generator generates the AC current signal on another frequency.

Special attention must also be devoted to the stability of voltage and frequency of the AC current signal since the signals to be acquired and to be evaluated are strongly affected by these factors. Trials have shown that for the voltage stability±0.2% and for the frequency stability±0.02% suffice.

In the following the invention will be explained in further detail in conjunction with a FIGURE.

The FIGURE shows schematically the measuring setup for remote monitoring and detecting coating defects on, for example, a cathodically protected underground pipe line.

An underground pipe line 1 is passively protected against corrosion by a coating 5 and actively by a fixedly installed cathodic protective current layout comprised of an anode 3 and a DC current generator 4.

The pipe line 1 is provided at intervals with monitoring units (RMU=Remote Monitoring System) 2, 2', also fixedly installed, which units, as will be described in the following, must fulfill several tasks.

The intervals between the monitoring units 2, 2' are inter alia determined by possible interference effects (for example stray currents, induced currents from power lines, bodies of flowing water, cathodic protective current, etc.). This means the greater the quantity and extent of the interference, the lower are chosen the intervals for the monitoring units. In the case of a disturbance-free laying of the pipe line, for example in a deserted area, the distance of the monitoring units can be more than 30 km, while in densely populated industrial areas the distance can be 5 or 10 km.

In the embodiment example depicted in the FIG. 1 each monitoring unit 2, 2' is according to the invention provided with an acquisition unit, not further depicted here, for the AC current signal, however, only every second monitoring unit 2 is provided with a signal generator for feeding in the AC current signal.

The monitoring units 2, 2', on the one hand, have the task of monitoring and controlling the cathodic protective current and, for another, the acquisition units integrated therein for the AC current signal have the task of acquiring the AC current signal, starting from the site of the impression, over the length of the pipe and of conducting the acquired and attenuated signal further to a central monitoring station.

In the present example the coating 5 of the pipe line 1 has a defect 6 on the right side, which defect effects an electric connection between pipe line and surrounding soil.

For the testing of pipe line 1 for coating defects, only one signal generator at a time of the pipe line is activated in order to exclude disturbing effects onto the measurement result by AC current signals of other active signal generators.

In the present example, as the AC current signal a sinusoidal AC current is superimposed onto the cathodic protective current by the signal generator of the left monitoring unit 2.

The acquisition unit of the monitoring unit 2' shows for an undamaged coating a normal trace of already converted frequency amplitudes of the AC current signal in the covered pipe line section, while the monitoring unit 2 depicted on the right acquires a markedly attenuated signal due to the current flowing via the coating defect 6 from the pipe line 1 to the ground.

The signal contour is acquired at every installed monitoring unit 2, 2' and conducted to the central monitoring station whereby, by comparison with previous measurements, the level of change of the attenuation is determined and therefrom the defect signal is derived. Since the location of the signal indication in relation to the line pipe section to be monitored can be well delimited, the defective pipe section can be quite accurately localized.

To appraise the damaged site and for the initiation of necessary repair measurements the exact localization is carried out onsite through suitable measures.

LIST OF REFERENCE NUMBERS

No. Designation
1 Pipe line
2 Monitoring unit with integrated signal generator
2' Monitoring unit without signal generator
3 Anode
4 Cathodic protective current
5 Coating
6 Coating defect

The invention claimed is:

1. A method for monitoring and detecting coating defects in a defined section of an underground or underwater coated pipe line, wherein the pipe line is provided section-wise at the ends of the particular section with a fixedly installed monitoring unit and comprising:
   application of an AC current signal at a clock cycle onto the pipe line, whose fixedly predetermined and stable frequency, taking into consideration the tolerance, is distinct in comparison to the frequencies measured within the scope of the monitoring of possible external interference signals,
   acquisition of the wave form of the AC current signal in the two terminal monitoring units of the particular section to be monitored for the determination of the distance-dependent attenuation level as a function of the distance of the signal from the site of the impression with this signal,
   conversion of the time-dependent signal into a frequency-dependent signal,
   determination of the frequency amplitudes corresponding to the frequency of the AC current signal,
   determination of the level of attenuation of the frequency amplitudes within the pipe line section to be monitored and comparison with comparison values previously determined in the two terminal monitoring units.

2. The method of claim 1, wherein
the frequency of the AC current signal is between 1 and 1000 Hz.

3. The method of claim 1,
wherein
in cathodically protected pipe lines the cathodic protective current is superimposed by the AC current signal and separately analyzed.

4. The method of claim 3, wherein
the AC current signal is applied independently in time of the cathodic protective current supplied permanently to the line section.

5. The method of claim 1,
wherein
the current form of the AC current signal is sinusoidal.

6. The method of claim 1,
wherein
the acquired measurement data of the AC current signal are conducted over wires to the central monitoring station.

7. The method of claim 1,
wherein
the acquired measurement data of the AC current signal are conducted wirelessly to the central monitoring station.

8. The method of claim 1,
wherein
the defined pipe line section has a length of one or several kilometers.

9. A device for monitoring and detecting coating defects in a defined section of one or several kilometers of an underground or underwater pipe line for carrying out the method of claim 1, wherein the pipe line is provided section-wise at the ends of the particular section with a fixedly installed monitoring unit for acquiring the AC current signal and the pipe line, as a function of the detectability and evaluatibility of the AC current signal, is provided at intervals with a signal generator.

10. The device of claim 9, wherein
the length of the pipe line between the signal generators is one or several pipe line sections, wherein at the particular measurement point in time the pipe line is impressed with only one AC current signal of an activated signal generator.

11. The device of claim 9, wherein
the length of the pipe line between the signal generators is one or several pipe line sections, wherein at the particular measurement point in time the pipe line is impressed with two or several AC current signals of different frequencies of, in each instance, two or several activated signal generators.

12. The device of claim 9,
wherein
the signal generators are integrated into the monitoring units.

13. The device of claim 9,
wherein
in the case of cathodically protected pipe lines the unit for the control and monitoring of the cathodic protective current is integrated into the monitoring unit for the AC current signal.

* * * * *